(12) United States Patent
Chae et al.

(10) Patent No.: US 11,884,693 B2
(45) Date of Patent: Jan. 30, 2024

(54) 1,3-ACETONEDICARBOXYLATE-DERIVED AMPHIPATHIC COMPOUNDS AND USES THEREOF

(71) Applicant: INDUSTRY-UNIVERSITY COOPERATION FOUNDATION HANYANG UNIVERSITY ERICA CAMPUS, Ansan-si (KR)

(72) Inventors: Pil Seok Chae, Ansan-si (KR); Ehsan Muhammad, Ansan-si (KR); Ho Jin Lee, Ansan-si (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 0 days.

(21) Appl. No.: 18/050,174

(22) Filed: Oct. 27, 2022

(65) Prior Publication Data
US 2023/0279039 A1    Sep. 7, 2023

(30) Foreign Application Priority Data

Mar. 2, 2022  (KR) .......................... 10-2022-0026674

(51) Int. Cl.
*C07H 15/04*    (2006.01)
*C07H 1/00*     (2006.01)

(52) U.S. Cl.
CPC ............... *C07H 15/04* (2013.01); *C07H 1/00* (2013.01)

(58) Field of Classification Search
CPC .................................. C07H 15/04; C07H 1/00
See application file for complete search history.

(56) References Cited

U.S. PATENT DOCUMENTS 8,530,631 B2 * 9/2013 Gellman ................ C07H 15/18
536/4.1
10,808,003 B2 * 10/2020 Chae ...................... C07H 15/24

OTHER PUBLICATIONS

Deckert et al. "The complete genome of the hyperthermophilic bacterium Aquifex aeolicus" Nature, 392:353-358 (1998).
Ethayathulla et al. "Structure-based mechanism for Na+/melibiose symport by MelB" Nature Communications, 5(3009):1-11 (2014).
Newstead et al. "Insights into outer membrane protein crystallization" Molecular Membrane Biology, 25(8):631-638 (2008).
Newstead et al. "Rationalizing alpha-helical membrane protein crystallization" Protein Science, 17:466-472 (2008).
Rosenbaum et al. "GPCR Engineering Yields High-Resolution Structural Insights into $\beta_2$-Adrenergic Receptor Function" Science, 318(5854):1266-1273 (2007).

* cited by examiner

*Primary Examiner* — Eric Olson
*Assistant Examiner* — Samuel L. Galster
(74) *Attorney, Agent, or Firm* — Myers Bigel, P.A.

(57) ABSTRACT

The present invention relates to: amphipathic compounds derived from 1,3-acetonedicarboxylate; a preparation method therefor; and a method for extracting, solubilizing, stabilizing, crystallizing or analyzing membrane proteins by using the same. In addition, the compound enables membrane proteins, which have various structures and characteristics, to be efficiently extracted from cell membranes and stably stored in an aqueous solution for a long time, compared to a conventional compound, thereby being usable in functional and structural analysis thereof. Analyzing the structure and function of membrane proteins is closely related to the development of a novel drug, and thus is one of the greatest interests in the biology and chemistry fields.

14 Claims, 7 Drawing Sheets

1,3-ACETONEDICARBOXYLATE-DERIVED AMPHIPATHIC COMPOUNDS AND USES THEREOF

CROSS-REFERENCE TO RELATED APPLICATION

This application claims priority to and the benefit of Korean Patent Application No. 10-2022-0026674, filed Mar. 2, 2022, the disclosure of which is incorporated herein by reference in its entirety.

TECHNICAL FIELD

The present invention relates to newly developed amphipathic compounds derived from 1,3-acetonedicarboxylate, a preparation method therefor; and a method for extracting, solubilizing, stabilizing, crystallizing or analyzing membrane proteins by using the same.

BACKGROUND ART

Membrane proteins play a crucial role in biological systems. Since these bio-macromolecules contain hydrophilic and hydrophobic moieties, amphiphilic molecules are required to extract membrane proteins from cell membranes and solubilize and stabilize the membrane proteins in an aqueous solution.

For structural analysis of membrane proteins, good-quality membrane protein crystals need to be obtained, and for this purpose, the structural stability of a membrane protein in an aqueous solution should take precedence. Although there are many existing amphiphilic molecules used in membrane protein research, with their number being 100 or more, only several amphiphilic molecules have been widely utilized in membrane protein structure research. These amphiphilic molecules include n-octyl-β-D-glucopyranoside (OG), n-nonyl-β-D-glucopyranoside (NG), n-decyl-β-D-maltopyranoside (DM), n-dodecyl-β-D-maltopyranoside (DDM), and lauryldimethylamine-N-oxide (LDAO) (Non-Patent Document 1, Non-Patent Document 2). However, since many membrane proteins surrounded by these molecules have their structure easily denatured or aggregated and thus tend to rapidly lose their functions, there are considerable limitations in the functional and structural studies of membrane proteins utilizing these molecules. This is because molecules in the related art cannot exhibit various properties due to their simple chemical structures. Therefore, there is a need for developing a new amphiphilic material having new and excellent properties through a new structure.

Thus, the present inventors have developed a class of amphipathic compounds derived from 1,3-acetonedicarboxylate (ACAs), and completed the present invention by confirming the membrane protein stabilizing properties of these compounds.

RELATED-ART DOCUMENTS

Non-Patent Documents

Non-Patent Document 1: S. Newstead et al., *Protein Sci.* 17 (2008) 466-472.

Non-Patent Document 2: S. Newstead et al., *Mol. Membr. Biol.* 25 (2008) 631-638.

Technical Problem

An object of the present invention is to provide a compound represented by Chemical Formula 1 or an isomer thereof.

Another object of the present invention is to provide a composition for extracting, solubilizing, stabilizing, crystallizing or analyzing a membrane protein, including the compound.

Still another object of the present invention is to provide a method for preparing the compound.

Yet another object of the present invention is to provide a method for extracting, solubilizing, stabilizing, crystallizing or analyzing a membrane protein, using the compound.

Technical Solution

The present invention provides a compound represented by the following Formula 1 or 2, or an isomer thereof:

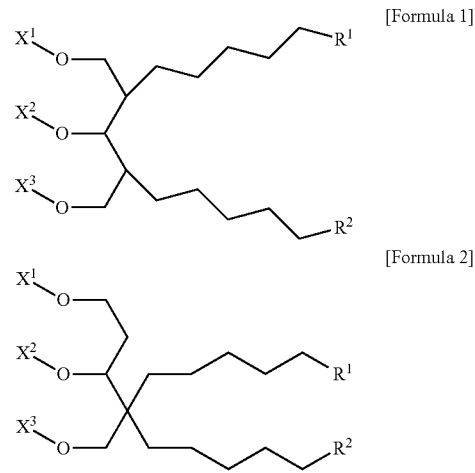

wherein:

$R^1$ or $R^2$ may be a substituted or unsubstituted $C_1$-$C_{15}$ alkyl group; and $X^1$ to $X^3$ may each be independently a saccharide.

As used herein, the term "saccharide" refers to a compound which has relatively small molecules among carbohydrates and is dissolved in water, and thus tastes sweet. Saccharides are classified into monosaccharides, disaccharides, and polysaccharides according to the number of molecules constituting a sugar. Here, the saccharide may act as a hydrophilic group.

The saccharide used in one exemplary embodiment may be a monosaccharide or a disaccharide. Specifically, the saccharide may be glucose or maltose, but is not limited thereto.

In Formula 1 or 2, the saccharides of $X^1$ to $X^3$ may act as a hydrophilic group. In addition, the alkyl groups of $R^1$ and $R^2$ may act as a hydrophobic group. Two alkyl chains and three saccharides were introduced into the compound according to an exemplary embodiment of the present invention in order to optimize the balance between hydrophilicity and hydrophobicity (hydrophile-lipophile balance).

Also, the compound according to one embodiment of the present invention is a symmetrical or asymmetrical amphipathic compound that is obtained by introducing two alkyl chains at the $2^{nd}$ and $5^{th}$ carbon atoms of 1,3-acetonedicarboxylate. A density of hydrophobic groups is maximized through the fluidity of a molecular structure of such a compound, and the geometrical structures of the molecules are modified to engineer a micelle structure, resulting in a significantly improved function of a self-assembly having such a nanostructure.

According to one specific embodiment of the present invention, $R^1$ and $R^2$ may each be independently a substituted or unsubstituted $C_3$-$C_{10}$ alkyl group; and $X^1$ to $X^3$ may each be independently glucose or maltose.

According to another specific embodiment of the present invention, $R^1$ and $R^2$ may be a substituted or unsubstituted $C_3$-$C_{10}$ alkyl group; and $X^1$ to $X^3$ may be glucose or maltose.

According to still another specific embodiment of the present invention, $R^1$ and $R^2$ may be an unsubstituted $C_3$-$C_{10}$ alkyl group; and $X^1$ to $X^3$ may be glucose.

The compound according to another exemplary embodiment of the present invention may be an amphiphilic molecule for extracting, solubilizing, stabilizing, crystallizing or analyzing a membrane protein, but is not limited thereto.

Specifically, the extraction may be extracting a membrane protein from a cell membrane.

As used herein, the term "amphiphilic molecule" refers to a molecule capable of having affinity for both polar and non-polar solvents because hydrophobic and hydrophilic groups coexist in a single molecule. Surfactants or phospholipid molecules present cell membrane are molecules having a hydrophilic group at one end and a hydrophobic group at the other end, and are characterized by being amphiphilic and forming micelles or liposomes in an aqueous solution. Although a hydrophilic group is polar, amphiphilic molecules thereof tend not to dissolve well in an aqueous solution because a non-polar group coexists. However, when the concentration is equal to or more than a certain threshold concentration (critical micelle concentration, CMC), hydrophobic interactions cause hydrophobic groups to gather inside, and round or oval micelles whose hydrophilic groups are exposed on the surface are formed, thereby greatly increasing solubility in water.

A method of measuring the CMC is not particularly limited, but a method widely known in the art may be used, and for example, the CMC may be measured by a fluorescent staining method using diphenylhexatriene (DPH).

The compound according to one exemplary embodiment of the present invention may have a critical micelle concentration (CMC) of 0.0001 to 1 mM, specifically 0.0001 to 0.1 mM, more specifically 0.001 to 0.1 mM, and even more specifically 0.001 to 0.02 mM in an aqueous solution, but the concentration is not limited thereto.

DDM, which is usually used for existing membrane protein research, has a critical micelle concentration of 0.17 mM. Compared to DDM the ACAs of the present exemplary embodiment have very small CMC values. Therefore, since micelles are easily formed even at low concentrations, membrane proteins can be effectively studied and analyzed using small amounts of ACAs, and thus ACAs may be advantageous in terms of utilization over DDM.

Also, another aspect of the present invention provides a composition for extracting, solubilizing, stabilizing, crystallizing, or analyzing a membrane protein including the compound.

Specifically, the extraction may include extracting a membrane protein from the cell membrane.

The composition may be in the form of micelles, liposomes, emulsions, or nanoparticles, but the present invention is not limited thereto.

The micelles may have a radius of 1.0 nm to 100 nm, specifically 2.0 nm to 20.0 nm, and more specifically 2 nm to 15 nm, but the micelle is not limited thereto.

A method of measuring the radius of the micelles is not particularly limited, but methods widely known in the related art may be used. For example, the radius of the micelles may be measured using a dynamic light scattering (DLS) experiment.

The micelles, liposomes, emulsions or nanoparticles may be bound to membrane proteins due to the internal hydrophobicity thereof. That is, the micelles, liposomes, emulsions or nanoparticles may extract and surround membrane proteins present in the cell membrane. Therefore, it is possible to extract, solubilize, stabilize, crystallize or analyze a membrane protein from a cell membrane by the micelle.

The composition may further include a buffer and the like which may be helpful for extracting, solubilizing, stabilizing, crystallizing or analyzing a membrane protein.

As used herein, the term "membrane protein" is a general term for proteins or glycoproteins which are introduced into cell membrane lipid bilayers. The membrane protein is present in various states such as passing through the entire layer of the cell membrane, being located on the surface layer, or lining the cell membrane. Examples of membrane proteins include enzymes, receptors such as peptide hormones and topical hormones, receptor carriers such as sugars, ion channels, cell membrane antigens, and the like.

The membrane protein includes any protein or glycoprotein introduced into cell membrane lipid bilayers, specifically, a leucine transporter (LeuT), a melibiose permease (MelB), a human β2 adrenergic receptor (β2AR), a mouse u-opioid receptor (MOR), or a combination of two or more thereof, but is not limited thereto.

As used herein, the term "solubilization of a membrane protein" means that a water-insoluble membrane protein is dissolved in a micelle in an aqueous solution.

As used herein, the term "stabilization of a membrane protein" means that a tertiary or quaternary structure is stably preserved such that the structure and function of the membrane protein is not changed.

As used herein, the term "crystallization of a membrane protein" means that crystals of the membrane protein are formed in a solution.

As used herein, the term "analysis of a membrane protein" means that the structure or function of the membrane protein is analyzed. In the exemplary embodiment, known methods may be used for the analysis of the membrane protein, and the method is not limited thereto, but the structure of the membrane protein may be analyzed using, for example, electron microscopy or nuclear magnetic resonance.

Still another aspect of the present invention provides a method of preparing a compound represented by Formula 1 according to the following Scheme 1, which includes:

1) allowing an alkyl halide to react with a compound of Formula 3, followed by reducing the reaction product to prepare a triol compound of Formula 4 (Step 1); and 2) introducing a saccharide to which a protecting group is attached into the compound of Formula 4 through a glycosylation reaction, followed by performing a deprotection reaction (Step 2):

[Scheme 1]

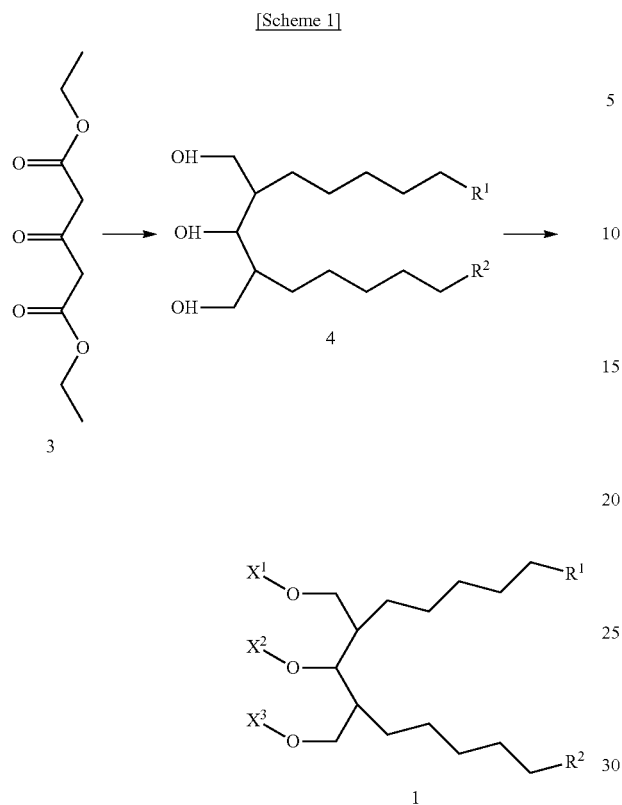

wherein:

$R^1$ or $R^2$ may be a substituted or unsubstituted $C_1$-$C_{15}$ alkyl group; and $X^1$ to $X^3$ may each be independently a saccharide.

According to one specific embodiment of the present invention, $R^1$ and $R^2$ may each be independently a substituted or unsubstituted $C_3$-$C_{15}$ alkyl group; and $X^1$ to $X^3$ may each be independently glucose or maltose.

According to another specific embodiment of the present invention, $R^1$ and $R^2$ may be a substituted or unsubstituted $C_3$-$C_{15}$ alkyl group; and $X^1$ to $X^3$ may be glucose or maltose.

According to still another specific embodiment of the present invention, $R^1$ and $R^2$ may be an unsubstituted $C_3$-$C_{15}$ alkyl group; and $X^1$ to $X^3$ may be glucose.

Yet another aspect of the present invention provides a method of preparing a compound represented by Formula 2 according to the following Scheme 2, which includes:

1) subjecting a compound of Formula 3 to an enolization reaction to prepare a compound of Formula 5 (Step 1);

2) allowing the compound of Formula 5 to react with an alkyl iodide to prepare a dialkylated compound of Formula 6 (Step 2);

3) isomerizing the compound of Formula 6 into a keto form to prepare a compound of Formula 7 (Step 3);

4) reducing the compound of Formula 7 to prepare a triol compound of Formula 8 (Step 4); and 5) introducing a saccharide to which a protecting group is attached into the compound of Formula 8 through a glycosylation reaction, followed by performing a deprotection reaction (Step 5):

[Scheme 2]

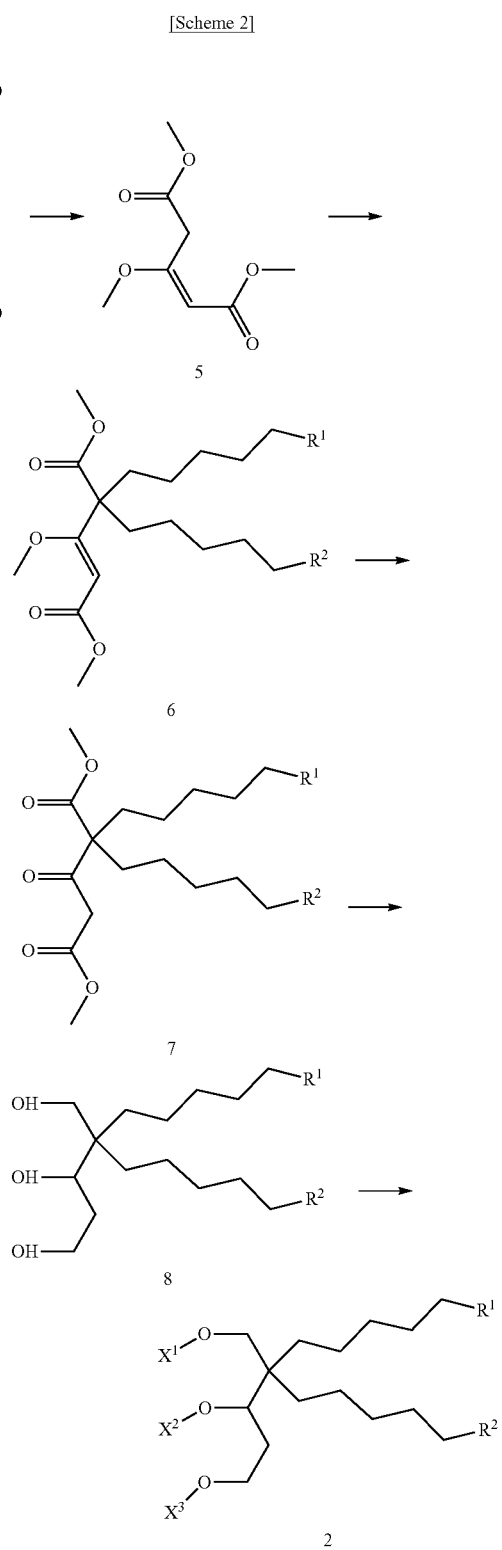

wherein:

$R^1$ or $R^2$ may be a substituted or unsubstituted $C_1$-$C_{15}$ alkyl group; and $X^1$ to $X^3$ may each be independently a saccharide.

According to one specific embodiment of the present invention, $R^1$ and $R^2$ may each be independently a substituted or unsubstituted $C_3$-$C_{15}$ alkyl group; and $X^1$ to $X^3$ may each be independently glucose or maltose.

According to another specific embodiment of the present invention, $R^1$ and $R^2$ may be a substituted or unsubstituted $C_3$-$C_{15}$ alkyl group; and $X^1$ to $X^3$ may be glucose or maltose.

According to still another specific embodiment of the present invention, $R^1$ and $R^2$ may be an unsubstituted $C_3$-$C_{15}$ alkyl group; and $X^1$ to $X^3$ may be glucose or maltose.

Advantageous Effects

When the 1,3-acetonedicarboxylate-derived compound according to exemplary embodiments of the present invention is used, a membrane protein can be stably stored in an aqueous solution for a long period of time compared to an existing compound, and can be utilized for the functional analysis and structural analysis thereof through this.

Since the structural and functional analysis of the membrane protein is one of the areas of greatest interest in biology and chemistry today, the compound can be applied to protein structure research closely related to new drug development.

Further, since the compound according to exemplary embodiments of the present invention is small in size during the formation of a complex with the membrane protein, good-quality membrane protein crystals can be obtained, thereby promoting the crystallization of the membrane protein.

In addition, the compound according to exemplary embodiments of the present invention can be synthesized from a starting material, which can be easily obtained, by a simple method, the compound for membrane protein research can be mass-produced.

MODES OF THE INVENTION

Hereinafter, the present invention will be described in detail with reference to examples thereof. However, it should be understood that the examples are for exemplary illustration and are not intended to limit the scope of the present invention. Those that can be easily inferred from the detailed description and examples of the present invention by those skilled in the art to which the present invention pertains are to be interpreted as falling within the scope of the present invention.

<Example 1> Synthesis Method of ACA-Ss

Figure 1:
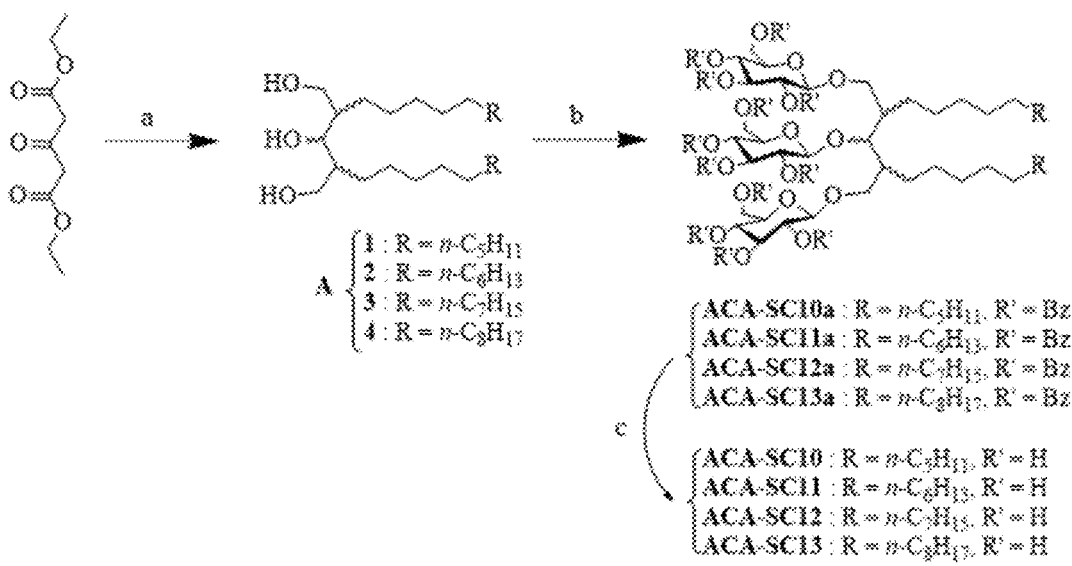
FIG. 1 is a diagram showing a synthesis scheme of ACA-As according to Example 1 of the present invention.

FIG. 1 illustrates the synthesis scheme of ACA-Ss. Four types of ACA-S compounds were synthesized by the following synthesis method.

<1-1> General Synthesis Procedure of Compound A (Step a of FIG. 1)

A mixture of diethyl 1,3-acetonedicarboxylate (1.0 eq.), alkyl iodide (2.0 eq.), and anhydrous $K_2CO_3$ (2.5 eq.) in anhydrous acetonitrile was stirred at room temperature for 10 minutes under an argon atmosphere, and then heated at 80° C. After the solvent was removed, the residue was dissolved in $CH_2Cl_2$, and washed with water and brine. The organic layer was dried over anhydrous $Na_2SO_4$, filtered, and concentrated under reduced pressure. The residue was purified by silica gel column chromatography (EtOAc/hexane) to obtain the desired compound, which was further treated with $LiAlH_4$ dissolved in THF at 0° C. The mixture was stirred at room temperature for 4 hours, sequentially quenched with MeOH, $H_2O$, and an aqueous 1.0 M HCl solution at 0° C., and then extracted with EtOAc. The mixed organic layer was washed with brine, and dried over anhydrous $Na_2SO_4$. The residue was purified by silica gel column chromatography (EtOAc/hexane) to obtain the target Compound A (A1, A2, A3, or A4) as a white solid.

<1-2> General Synthesis Procedure for Glycosylation Reaction (Step b of FIG. 1)

A mixture of Compound A (1 eq.) and AgOTf (4.5 eq.) was stirred in anhydrous $CH_2Cl_2$ at −45° C. A solution of perbenzoylated glucosylbromide in anhydrous $CH_2Cl_2$ was added dropwise to this suspension. Stirring was continued for 0.5 hr at −45° C., and let the reaction mixture warm to 0° C. and left stirring for 1 hr. After completion, pyridine was added to the reaction mixture, and it was diluted with $CH_2Cl_2$ before being filtered through celite. The filtrate was washed with a 1.0 M aqueous $Na_2S_2O_3$, a 0.1 M aqueous HCl solution, and brine. The organic layer was dried with anhydrous $Na_2SO_4$, and the solvent was removed by rotary evaporation. The residue was purified by silica gel column chromatography (EtOAc/hexane), which provided the desired glycosylated product as a white solid.

<1-3> General Synthesis Procedure for Deprotection Reaction (Step c of FIG. 1)

The O-protected glycosylated compound was dissolved in MeOH and the required amount of a methanolic solution of 0.5 M NaOMe was added so that the total concentration of NaOMe could be 0.05 M. The reaction mixture was stirred for 12 h at room temperature, and then neutralized with Amberlite IR-120 resin ($H^+$ form). The resin was removed by filtration and washed with MeOH. The solvent was removed by rotary evaporation followed by in vacuo. The residue was purified by silica gel column chromatography (eluting with MeOH/$CH_2Cl_2$) and recrystallization using $CH_2Cl_2$/MeOH/diethyl ether. The desired deprotected product was provided as a white solid.

<Preparation Example 1> Synthesis of ACA-SC10

<1-1> Synthesis of Compound A1

Compound A1 was synthesized with a yield of 72% according to Example 1-1. $^1$H NMR (400 MHz, $CDCl_3$): δ

4.24 (br s, 1H), 3.88-3.66 (m, 5H), 3.43 (br s, 2H), 1.74-1.58 (m, 2H), 1.48-1.20 (m, 36H), 0.88 (t, J=7.6 Hz, 6H); $^{13}$C NMR (100 MHz, CDCl$_3$): δ 64.9, 64.2, 62.8, 42.8, 41.9, 41.5, 32.0, 30.4, 30.1, 29.9, 29.8, 29.7, 29.5, 28.1, 28.0, 27.9, 27.1, 25.7, 23.7, 22.8, 14.2.

<1-2> Synthesis of ACA-SC10a

ACA-SC10a was synthesized with a yield of 85% according to Example 1-2. $^1$H NMR (400 MHz, CDCl$_3$): δ 8.16-7.82 (m, 24H), 7.56-7.20 (m, 36H), 5.88-5.62 (m, 4H), 5.54-5.38 (m, 4H), 4.73-4.10 (m, 10H), 3.86-3.78 (m, 2H), 3.71-3.59 (m, 2H), 3.23-3.16 (m, 1H), 1.72-1.68 (m, 2H), 1.38-1.07 (m, 36H), 0.88 (t, J=7.6 Hz, 6H); $^{13}$C NMR (100 MHz, CDCl$_3$): δ 166.2, 165.9, 165.3, 165.0, 164.9, 164.8, 164.7, 133.4, 133.2, 133.1, 129.9, 129.6, 129.2, 129.0, 128.8, 128.6, 101.5, 101.3, 101.0, 72.7, 72.2, 69.9, 63.0, 32.1, 30.3, 29.9, 29.8, 29.7, 29.5, 28.1, 28.0, 27.8, 27.1, 25.7, 23.7, 22.8, 14.3.

<1-3> Synthesis of ACA-SC10

Compound ACA-SC10 was synthesized with a yield of 94% according to Example 1-3. $^1$H NMR (400 MHz, CD$_3$OD): δ 4.61 and 4.54 (d, J=8.0 Hz, 1H), 4.48-4.26 (m, 2H), 4.18-3.96 (m, 3H), 3.88-3.82 (m, 4H), 3.71-3.60 (m, 4H), 3.43-3.15 (m, 14H), 2.05-1.80 (m, 2H), 1.46-1.20 (m, 36H), 0.89 (t, J=7.6 Hz, 6H); $^{13}$C NMR (100 MHz, CD$_3$OD): δ 105.3, 104.9, 104.8, 104.7, 104.4, 104.3, 104.2, 104.1, 103.8, 79.7, 78.3, 78.2, 78.1, 78.0, 77.8, 77.0, 75.8, 75.7, 75.2, 75.1, 75.0, 72.1, 71.7, 71.6, 71.5, 71.4, 63.1, 62.9, 62.8, 43.7, 42.7, 42.5, 42.4, 41.8, 40.5, 33.2, 31.0, 30.9, 30.8, 30.7, 30.6, 23.8, 14.6; HRMS (FAB): calcd. for C$_{43}$H$_{82}$O$_{18}$Na$^+$ [M+Na]$^+$ 909.5399, found 909.5401.

<Preparation Example 2> Synthesis of ACA-SC11

<2-1> Synthesis of Compound A2

Compound A2 was synthesized with a yield of 72% according to Example 1-1. $^1$H NMR (400 MHz, CDCl$_3$): δ 4.24 (br s, 1H), 3.87-3.66 (m, 5H), 3.43 (br s, 2H), 1.74-1.58 (m, 2H), 1.48-1.20 (m, 40H), 0.87 (t, J=7.6 Hz, 6H); $^{13}$C NMR (100 MHz, CDCl$_3$): δ 64.9, 64.3, 62.7, 42.7, 41.9, 41.5, 32.1, 30.4, 30.2, 29.9, 29.8, 29.7, 29.5, 28.0, 27.9, 27.1, 22.6, 14.2.

<2-2> Synthesis of ACA-SC11a

ACA-SC11a was synthesized with a yield of 85% according to Example 1-2. $^1$H NMR (400 MHz, CDCl$_3$): δ 8.12-7.82 (m, 24H), 7.55-7.20 (m, 36H), 5.88-5.62 (m, 4H), 5.54-5.38 (m, 4H), 4.73-4.10 (m, 10H), 3.86-3.78 (m, 2H), 3.71-3.59 (m, 2H), 3.23-3.16 (m, 1H), 1.72-1.68 (m, 2H), 1.38-1.07 (m, 40H), 0.87 (t, J=7.6 Hz, 6H); $^{13}$C NMR (100 MHz, CDCl$_3$): δ 166.2, 165.9, 165.3, 165.0, 164.9, 164.8, 164.7, 133.4, 133.1, 129.9, 129.6, 129.2, 129.0, 128.8, 128.6, 101.5, 101.3, 101.0, 72.7, 72.2, 69.9, 63.0, 42.6, 41.7, 41.3, 32.1, 30.3, 30.1, 29.9, 29.8, 29.7, 29.5, 28.0, 27.7, 27.1, 22.6, 14.3.

<2-3> Synthesis of ACA-SC11

Compound ACA-SC11 was synthesized with a yield of 94% according to Example 1-3. $^1$H NMR (400 MHz, CD$_3$OD): δ 4.61 and 4.54 (d, J=8.0 Hz, 1H), 4.48-4.26 (m, 2H), 4.19-3.95 (m, 3H), 3.88-3.82 (m, 4H), 3.71-3.60 (m, 4H), 3.43-3.15 (m, 14H), 2.05-1.80 (m, 2H), 1.46-1.20 (m, 40H), 0.89 (t, J=7.6 Hz, 6H); $^{13}$C NMR (100 MHz, CD$_3$OD): δ 105.4, 104.9, 104.8, 104.7, 104.4, 104.2, 78.3, 78.1, 78.0, 77.9, 77.4, 77.1, 75.8, 75.2, 75.1, 75.0, 72.1, 71.8, 71.6, 71.5, 71.2, 62.8, 43.7, 42.6, 42.5, 41.8, 33.2, 31.2, 31.0, 30.9, 30.8, 30.7, 29.2, 23.8, 14.6; HRMS (FAB): calcd. for C$_{45}$H$_{86}$O$_{18}$Na$^+$ [M+Na]$^+$ 937.5712, found 937.5709.

<Preparation Example 3> Synthesis of ACA-SC12

<3-1> Synthesis of Compound A3

Compound A3 was synthesized with a yield of 72% according to Example 1-1. $^1$H NMR (400 MHz, CDCl$_3$): δ 4.22 (br s, 1H), 3.86-3.65 (m, 5H), 3.40 (br s, 2H), 1.74-1.58 (m, 2H), 1.48-1.20 (m, 44H), 0.87 (t, J=7.6 Hz, 6H); $^{13}$C NMR (100 MHz, CDCl$_3$): δ 64.8, 64.4, 62.7, 42.7, 41.9, 41.5, 32.1, 30.4, 30.2, 29.9, 29.8, 29.7, 28.0, 27.9, 27.3, 22.5, 14.2.

<3-2> Synthesis of ACA-SC12a

ACA-SC12a was synthesized with a yield of 85% according to Example 1-2. $^1$H NMR (400 MHz, CDCl$_3$): δ 8.14-7.82 (m, 24H), 7.55-7.20 (m, 36H), 5.88-5.62 (m, 4H), 5.54-5.38 (m, 4H), 4.73-4.10 (m, 10H), 3.86-3.78 (m, 2H), 3.71-3.59 (m, 2H), 3.23-3.16 (m, 1H), 1.72-1.68 (m, 2H), 1.38-1.07 (m, 44H), 0.88 (t, J=7.6 Hz, 6H); $^{13}$C NMR (100 MHz, CDCl$_3$): δ 166.1, 165.8, 165.3, 165.0, 164.8, 164.8, 164.6, 133.4, 133.2, 129.9, 129.6, 129.3, 129.0, 128.8, 128.6, 101.5, 101.3, 101.0, 72.7, 72.2, 69.9, 63.0, 42.6, 41.9, 41.5, 32.1, 30.4, 30.2, 29.9, 29.8, 29.6, 28.0, 27.8, 27.2, 22.4, 14.3.

<3-3> Synthesis of ACA-SC12

Compound ACA-SC12 was synthesized with a yield of 94% according to Example 1-3. $^1$H NMR (400 MHz, CD$_3$OD): δ 4.60 and 4.54 (d, J=8.0 Hz, 1H), 4.48-4.26 (m, 2H), 4.19-3.95 (m, 3H), 3.88-3.82 (m, 4H), 3.71-3.58 (m, 4H), 3.43-3.15 (m, 14H), 2.04-1.80 (m, 2H), 1.46-1.20 (m, 44H), 0.89 (t, J=7.6 Hz, 6H); $^{13}$C NMR (100 MHz, CD$_3$OD): δ 105.0, 104.9, 104.8, 104.5, 104.3, 79.9, 78.4, 78.2, 78.1, 78.0, 77.2, 75.8, 75.2, 75.1, 71.8, 71.7, 71.6, 63.0, 62.8, 33.2, 31.0, 30.9, 30.6, 23.8, 14.6; HRMS (FAB): calcd. for C$_{47}$H$_{90}$O$_{18}$Na$^+$ [M+Na]$^+$ 965.6025, found 965.6023.

<Preparation Example 4> Synthesis of ACA-SC13

<4-1> Synthesis of Compound A4

Compound A4 was synthesized with a yield of 72% according to Example 1-1. $^1$H NMR (400 MHz, CDCl$_3$): δ 4.24 (br s, 1H), 3.86-3.65 (m, 5H), 3.40 (br s, 2H), 1.74-1.58 (m, 2H), 1.48-1.20 (m, 48H), 0.88 (t, J=7.6 Hz, 6H); $^{13}$C NMR (100 MHz, CDCl$_3$): δ 65.6, 64.9, 63.3, 42.7, 41.9, 41.4, 32.1, 30.4, 30.2, 29.9, 29.8, 29.7, 29.6, 28.2, 27.9, 27.1, 25.6, 23.4, 22.8, 14.3.

<4-2> Synthesis of ACA-SC13a

ACA-SC13a was synthesized with a yield of 85% according to Example 1-2. $^1$H NMR (400 MHz, CDCl$_3$): δ 8.16-7.82 (m, 24H), 7.55-7.20 (m, 36H), 5.88-5.62 (m, 4H), 5.54-5.38 (m, 4H), 4.73-4.10 (m, 10H), 3.86-3.78 (m, 2H), 3.71-3.59 (m, 2H), 3.23-3.16 (m, 1H), 1.72-1.68 (m, 2H), 1.36-1.08 (m, 48H), 0.88 (t, J=7.6 Hz, 6H); $^{13}$C NMR (100

MHz, CDCl$_3$): δ 166.1, 165.8, 165.3, 165.0, 164.8, 164.8, 164.6, 133.4, 133.2, 129.9, 129.6, 129.3, 129.0, 128.8, 128.6, 101.5, 101.3, 101.0, 72.5, 72.2, 69.9, 63.3, 42.7, 41.9, 41.4, 32.1, 30.4, 30.2, 29.9, 29.8, 29.5, 28.3, 27.8, 27.1, 25.4, 23.3, 22.7, 14.2.

<4-3> Synthesis of ACA-SC13

Compound ACA-SC13 was synthesized with a yield of 94% according to Example 1-3. $^1$H NMR (400 MHz, CD$_3$OD): δ 4.60 and 4.54 (t, J=8.0 Hz, 1H), 4.48-4.25 (m, 2H), 4.19-3.95 (m, 3H), 3.88-3.82 (m, 4H), 3.73-3.58 (m, 4H), 3.43-3.15 (m, 14H), 2.04-1.80 (m, 2H), 1.46-1.20 (m, 48H), 0.89 (t, J=7.6 Hz, 6H); $^{13}$C NMR (100 MHz, CD$_3$OD): δ 105.4, 104.9, 104.8, 104.7, 104.4, 104.2, 104.1, 103.8, 78.3, 78.2, 78.1, 78.0, 77.9, 77.4, 71.1, 75.8, 75.2, 75.0, 72.5, 72.1, 71.8, 71.6, 71.5, 71.4, 71.3, 63.2, 62.8, 33.2, 31.3, 31.0, 30.9, 30.6, 23.8, 14.6; HRMS (FAB): calcd. for C$_{49}$H$_{94}$O$_{18}$Na$^+$ [M+Na]$^+$ 993.6338, found 993.6342.

<Example 2> Synthesis Method of ACA-As

FIG. 1 illustrates the synthesis scheme of ACA-As. Four types of ACA-A compounds were synthesized according to the following synthesis method.

Figure 2:
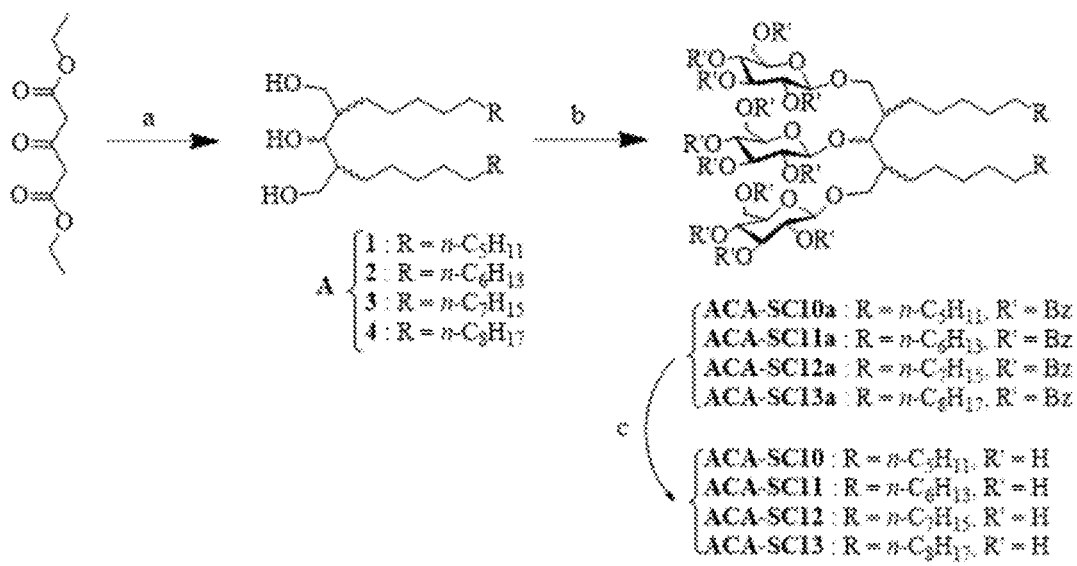
FIG. 2 is a diagram showing a synthesis scheme of ACAs-Ss according to Example 2 of the present invention.

<2-1> Synthesis Procedure of Dimethyl (E)-3-methoxypent-2-enedioate (Step a of FIG. 2)

A mixture including dimethyl 1,3-acetonedicarboxylate (1.0 eq.), trimethyl orthoformate (0.63 eq.), and a catalytic amount of p-toluenesulfonic acid in anhydrous MeOH was refluxed for 40 hours. The mixture was diluted with ethyl acetate, and washed with an aqueous 0.5 M Na$_2$CO$_3$ solution and brine. The organic layer was dried over anhydrous Na$_2$SO$_4$, and the solvent was removed using a rotary evaporator. The residue was purified by silica gel column chromatography (EtOAc/hexane) to obtain Compound B with a yield of 56%. 1H NMR (400 MHz, CDCl$_3$): δ 5.20 (s, 1H), 3.84 (s, 2H), 3.71 (s, 3H), 3.69 (s, 3H), 3.68 (s, 3H); $^{13}$C NMR (100 MHz, CDCl$_3$): δ 169.45, 168.05, 167.66, 92.95, 55.90, 52.06, 50.98, 38.10.

<2-2> Synthesis of Dialkylated Compound C (Step b of FIG. 2)

A mixture of Compound B (1.0 eq.), alkyl iodide (3.0 eq.), and NaH (2.5 eq.) in anhydrous DMF was stirred at 60° C. for 5 hours. The mixture was extracted with diethyl ether, and washed with an aqueous 1.0 M HCl solution and brine. The organic layer was collected, dried over anhydrous Na$_2$SO$_4$, and concentrated under reduced pressure. The residue was purified by silica gel column chromatography (EtOAc/hexane) to obtain the target Compound C.

<2-3> Synthesis of Dialkylated Compound D (Step c of FIG. 2)

Compound C (1.0 eq.) was dissolved in a 1:1 solution of formic acid (88%, 20.0 eq.) and hexane. The mixture was refluxed for 40 hours, and the reaction mixture was then carefully poured in an aqueous 1.0 M Na$_2$CO$_3$ solution and extracted with diethyl ether. The organic layer was collected, washed with brine, and dried over anhydrous Na$_2$SO$_4$. The solvent was removed by rotary evaporation, and the residue was purified by silica gel column chromatography (EtOAc/hexane) to obtain a dialkylated ester derivative (Compound D) as a product.

<2-4> General Synthesis Procedure of Dialkylated Triol Derivative (Step d of FIG. 2)

Compound D (1.0 eq.) was dissolved in anhydrous THF, and treated with LiAlH$_4$ (3.5 eq.) while stirring at 70° C. for 5 hours. The reaction mixture was sequentially quenched with MeOH, H$_2$O, and an aqueous 1.0 M HCl solution, and then extracted with diethyl ether. The organic layer was collected, washed with brine, and dried over anhydrous Na$_2$SO$_4$. The solvent was removed by rotary evaporation, and the residue was purified silica gel column chromatography (EtOAc/hexane) to obtain a dialkylated triol derivative (Compound E) as a product.

<2-5> General Synthesis Procedure for Glycosylation Reaction (Step e of FIG. 2)

A mixture of Compound E (1 eq.) and AgOTf (3.6 eq.) in anhydrous CH$_2$Cl$_2$ was stirred at −45° C. under an N$_2$ atmosphere. Thereafter, perbenzoylated maltosyl bromide (3.6 eq.) dissolved in CH$_2$Cl$_2$ was added to the suspension. The suspension was stirred at −45° C. for 5 minutes, and then stirred at 0° C. for 30 minutes. After the reaction was completed (detected by TLC), pyridine was added to the reaction mixture. The reaction mixture was diluted with CH$_2$Cl$_2$ (30 mL), and then filtered through Celite. The filtrate was sequentially washed with an aqueous 1.0 M Na$_2$S$_2$O$_3$ solution, an aqueous 0.1 M HCl solution, and brine. Then, the organic layer was dried over anhydrous Na$_2$SO$_4$, and the solvent was removed by rotary evaporation. The resulting residue was purified by silica gel column chromatography (EtOAc/hexane) to obtain the glycosylated target compound.

<2-6> General Synthesis Procedure for Deprotection Reaction (Step f of FIG. 2)

The O-protected glycosylated compound was dissolved in MeOH and the required amount of a methanolic solution of 0.5 M NaOMe was added so that the total concentration of NaOMe could be 0.05 M. The reaction mixture was stirred for 12 h at room temperature, and then neutralized with Amberlite IR-120 resin (H$^+$ form). The resin was removed by filtration and washed with MeOH. The solvent was removed by rotary evaporation followed by in vacuo. The residue was purified by silica gel column chromatography (eluting with MeOH/CH$_2$Cl$_2$) and recrystallization using CH$_2$Cl$_2$/MeOH/diethyl ether. The desired deprotected compound was provided as a white solid.

<Preparation Example 5> Synthesis of ACA-AC10

<5-1> Synthesis of Compound C1

Compound C1 was synthesized with a yield of 55% according to Examples 2-1 and 2-2. $^1$H NMR (400 MHz, CDCl$_3$): δ 5.20 (s, 1H), 3.89 (s, 3H), 3.70 (s, 3H), 3.68 (s, 3H), 1.77-1.69 (m, 4H), 1.32-1.25 (m, 28H), 1.19-1.12 (m, 2H), 1.06-0.99 (m, 2H), 0.88 (t, J=6.8 Hz, 6H); $^{13}$C NMR (100 MHz, CDCl$_3$): δ 174.04, 173.61, 165.44, 96.93, 62.91, 57.38, 52.05, 51.17, 31.94, 31.91, 29.93, 29.71, 29.69, 29.66, 29.61, 29.48, 29.40, 29.38, 23.81, 22.71, 14.13.

<5-2> Synthesis of Compound D1

Compound D1 was synthesized with a yield of 72% according to Example 2-3. $^1$H NMR (400 MHz, CDCl$_3$): δ 3.73 (s, 3H), 3.72 (s, 3H), 3.49 (s, 2H), 1.94-1.75 (m, 4H), 1.32-1.25 (m, 28H), 1.13-1.03 (m, 4H), 0.88 (t, J=6.8 Hz, 6H); $^{13}$C NMR (100 MHz, CDCl$_3$): δ 199.92, 172.60, 167.23, 63.89, 52.39, 52.34, 45.79, 31.92, 31.61, 29.90, 29.62, 29.55, 29.34, 29.31, 23.79, 22.71, 14.12.

<5-3> Synthesis of Compound E1

Compound E1 was synthesized with a yield of 71% according to Example 2-4. $^1$H NMR (400 MHz, CDCl$_3$): δ 4.20 (br s, 1H), 3.94 (m, 1H), 3.87 (m, 2H), 3.70 (d, 1H), 3.54 (d, 1H), 3.34 (br s, 2H), 1.77 (m, 1H), 1.70 (br d, 1H), 1.54 (m, 2H), 1.26-0.99 (m, 34H), 0.88 (t, J=6.8 Hz, 6H); $^{13}$C NMR (100 MHz, CDCl$_3$): δ 79.48, 68.17, 63.21, 42.47, 32.51, 31.94, 31.14, 30.94, 30.66, 29.71, 29.67, 29.54, 29.37, 22.93, 22.71, 14.13.

<5-4> Synthesis of ACA-AC10a

ACA-AC10a was synthesized with a yield of 56% according to Example 2-5. $^1$H NMR (400 MHz, CDCl$_3$): δ 8.32-7.78 (m, 24H), 7.59-7.19 (m, 36H), 6.21 (t, J=9.6 Hz, 1H), 5.95 (t, J=9.6 Hz, 1H), 5.86 (t, J=9.6 Hz, 1-1), 5.80-5.57 (m, 4H), 5.54-5.41 (m, 4H ), 4.68-4.39 (m, 10H), 4.36-4.31 (m, 1H), 4.26-4.21 (m, 1H), 4.06-3.96 (m, 2H), 3.96-3.88 (m, 1H), 3.81-3.75 (m, 1H), 1.85-1.77 (m, 1H), 1.74-1.64 (m, 1H), 1.34-1.08 (m, 36H ), 0.88 (t, J=6.8 Hz, 6H); $^{13}$C NMR (100 MHz, CDCl$_3$): δ 166.09, 166.05, 166.0, 165.85, 165.81, 165.80, 165.19, 165.16, 164.79, 164.76, 133.55, 133.51, 133.43, 133.27, 133.16, 133.09, 132.99, 130.04, 129.85, 129.77, 129.66, 129.46, 128.83, 129.51, 128.43, 128.37, 128.35, 101.82, 101.60, 101.25, 101.01, 100.92, 73.21, 73.11, 72.84, 72.75, 72.31, 72.15, 72.07, 71.99, 71.89, 71.71, 71.50, 70.04, 69.91, 69.74, 69.39, 63.41, 63.32, 62.99, 62.55, 32.10, 30.68, 30.52, 29.85, 29.82, 29.79, 29.73, 29.69, 29.58, 29.54, 29.79, 29.48, 23.66, 23.31, 22.75, 14.20.

<5-5> Synthesis of ACA-AC10

ACA-AC10 was synthesized with a yield of 88% according to Example 2-6. $^1$H NMR (400 MHz, CD$_3$OD): δ 4.56 and 4.51 (d, J=8.0 Hz, 1H), 4.32 and 4.23 (d, J=8.0 Hz, 2H), 4.19-4.02 (m, 3H), 3.93-3.83 (m, 4H), 3.71-3.59 (m, 4H), 3.41-3.14 (m, 14H), 2.05-1.87 and 1.76-1.68 (m, 2H), 1.48-1.20 (m, 36H), 0.90 (t, J=6.8 Hz, 6H); $^{13}$C NMR (100 MHz, CD$_3$OD): δ 105.37, 104.47, 104.45, 104.27, 104.0, 104.3, 103.97, 81.22, 80.0, 78.39, 78.27, 78.15, 78.04, 77.99, 77.91, 77.16, 77.11, 75.90, 75.79, 75.25, 75.08, 75.0, 74.89, 74.49, 72.73, 72.27, 71.89, 71.72, 71.66, 71.57, 69.07, 67.60, 63.42, 63.03, 62.80, 45.23, 44.58, 33.13, 32.67, 32.49, 32.12, 32.01, 31.87, 30.91, 30.89, 30.83, 30.80, 30.73, 30.55, 30.54, 25.0, 24.68, 24.62, 24.31, 24.24, 23.77, 14.50; HRMS (FAB): calcd. for C$_{43}$H$_{82}$O$_{18}$Na$^+$ [M+Na]$^+$ 909.5399, found 909.5396.

<Preparation Example 6> Synthesis of ACA-AC11

<6-1> Synthesis of Compound C2

Compound C2 was synthesized with a yield of 54% according to Examples 2-1 and 2-2. $^1$H NMR (400 MHz, CDCl$_3$): δ 5.19 (s, 1H), 3.90 (s, 3H), 3.70 (s, 3H), 3.68 (s, 3H), 1.77-1.69 (m, 4H), 1.32-1.25 (m, 32H), 1.19-1.12 (m, 2H), 1.06-0.98 (m, 2H), 0.88 (t, J=6.8 Hz, 6H); $^{13}$C NMR (100 MHz, CDCl$_3$): δ 174.04, 173.62, 165.43, 96.93, 62.90, 57.38, 52.04, 51.17, 31.94, 31.91, 29.92, 29.71, 29.69, 29.67, 29.65, 29.61, 29.48, 29.41, 29.38, 23.81, 22.70, 14.13.

<6-2> Synthesis of Compound D2

Compound D2 was synthesized with a yield of 43% according to Example 2-3. $^1$H NMR (400 MHz, CDCl$_3$): δ 3.73 (s, 3H), 3.72 (s, 3H), 3.49 (s, 2H), 1.94-1.75 (m, 4H), 1.32-1.25 (m, 32H), 1.13-1.03 (m, 4H), 0.88 (t, J=6.8 Hz, 6H); $^{13}$C NMR (100 MHz, CDCl$_3$): δ 199.93, 172.60, 167.23, 63.89, 52.38, 52.34, 45.79, 31.92, 31.60, 29.90, 29.63, 29.55, 29.35, 29.31, 23.79, 22.70, 14.12.

<6-3> Synthesis of Compound E2

Compound E2 was synthesized with a yield of 70% according to Example 2-4. $^1$H NMR (400 MHz, CDCl$_3$): δ 3.94 (m, 1H), 3.88 (m, 2H), 3.72 (d, 1H), 3.56 (d, 1H), 2.83 (br s, 2H), 1.80 (m, 1H), 1.71 (br d, 1H), 1.52 (m, 2H), 1.26-0.98 (m, 38H), 0.88 (t, J=6.8 Hz, 6H); $^{13}$C NMR (100 MHz, CDCl$_3$): δ 79.49, 68.17, 63.21, 42.47, 32.49, 31.93, 31.14, 30.94, 30.65, 29.71, 29.67, 29.54, 29.35, 22.93, 22.71, 14.13.

<6-4> Synthesis of ACA-AC11a

ACA-AC11a was synthesized with a yield of 61% according to Example 2-5. $^1$H NMR (400 MHz, CDCl$_3$): δ 8.28-7.77 (m, 24H), 7.57-7.21 (m, 36H), 6.16 (t, J=9.6 Hz, 1H), 5.91 (t, J=9.6 Hz, 1H), 5.82 (t, J=9.6 Hz, 1H), 5.76-5.54 (m, 4H), 5.50-5.37 (m, 4H), 4.63-4.35 (m, 10H), 4.30-4.27 (m, 1H), 4.23-4.17 (m, 1H), 4.01-3.92 (m, 2H), 3.88-3.84 (m, 1H), 3.79-3.71 (m, 1H), 1.77-1.72 (m, 1H), 1.69-1.54 (m, 1H), 1.34-1.05 (m, 40H), 0.88 (t, J=6.8 Hz, 6H); $^{13}$C NMR (100 MHz, CDCl$_3$): δ 166.07, 166.03, 165.85, 165.81, 165.19, 165.16, 164.79, 164.76, 133.55, 133.51, 133.43, 133.27, 133.16, 133.09, 132.99, 130.04, 129.85, 129.77, 129.66, 129.46, 128.83, 129.51, 128.43, 128.33, 101.82, 101.60, 101.23, 101.01, 100.92, 73.21, 73.11, 72.84, 72.75, 72.31, 72.15, 72.07, 71.99, 71.89, 71.71, 71.50, 70.04, 69.91, 69.74, 69.39, 63.41, 63.32, 62.94, 62.55, 32.10, 30.68, 30.52, 29.85, 29.79, 29.71, 29.69, 29.55, 29.51, 29.79, 29.48, 23.66, 23.31, 22.75, 14.20.

<6-5> Synthesis of ACA-AC11

ACA-AC11 was synthesized with a yield of 83% according to Example 2-6. $^1$H NMR (400 MHz, CD$_3$OD): δ 4.56 and 4.51 (d, J=8.0 Hz, 1H), 4.32 and 4.22 (d, J=8.0 Hz, 2H), 4.18-4.03 (m, 3H), 3.93-3.83 (m, 4H), 3.71-3.60 (m, 4H), 3.41-3.14 (m, 14H), 2.05-1.87 and 1.75-1.66 (m, 2H), 1.48-1.16 (m, 40H), 0.90 (t, J=6.8 Hz, 6H); $^{13}$C NMR (100 MHz, CD$_3$OD): δ 105.38, 104.45, 104.29, 104.01, 81.24, 80.02, 78.41, 78.28, 78.15, 78.06, 78.0, 77.92, 77.16, 75.91, 75.80, 75.25, 75.09, 75.0, 74.50, 72.28, 71.90, 71.73, 71.67, 71.58, 69.10, 67.61, 63.42, 63.30, 63.02, 62.85, 45.25, 44.59, 33.13, 32.66, 32.50, 32.11, 32.0, 31.93, 31.87, 30.88, 30.85, 30.80, 30.73, 30.55, 25.0, 24.68, 24.31, 23.78, 14.50; HRMS (FAB): calcd. for C$_{45}$H$_{86}$O$_{18}$Na$^+$ [M+Na]$^+$ 937.5712, found 937.5711.

<Preparation Example 7> Synthesis of ACA-AC12

<7-1> Synthesis of Compound C3

Compound C3 was synthesized with a yield of 42% according to Examples 2-1 and 2-2. $^1$H NMR (400 MHz, CDCl$_3$): δ 5.19 (s, 1H), 3.90 (s, 3H), 3.70 (s, 3H), 3.68 (s, 3H), 1.77-1.69 (m, 4H), 1.32-1.25 (m, 36H), 1.19-1.11 (m, 2H), 1.06-0.98 (m, 2H), 0.88 (t, J=6.8 Hz, 6H); $^{13}$C NMR (100 MHz, CDCl$_3$): δ 174.04, 173.62, 165.43, 96.92, 62.90, 57.38, 52.05, 51.17, 31.94, 31.91, 29.91, 29.72, 29.69, 29.67, 29.64, 29.61, 29.47, 29.41, 29.38, 23.81, 22.70, 14.14.

<7-2> Synthesis of Compound D3

Compound D3 was synthesized with a yield of 63% according to Example 2-3. $^1$H NMR (400 MHz, CDCl$_3$): δ 3.73 (s, 3H), 3.72 (s, 3H), 3.49 (s, 2H), 1.94-1.75 (m, 4H), 1.32-1.25 (m, 36H), 1.13-1.04 (m, 4H), 0.88 (t, J=6.8 Hz, 6H); $^{13}$C NMR (100 MHz, CDCl$_3$): δ 199.93, 172.60, 167.22, 63.89, 52.37, 52.33, 45.79, 31.93, 31.60, 29.90, 29.63, 29.54, 29.41, 29.36, 29.31, 23.78, 22.70, 14.12.

<7-3> Synthesis of Compound E3

Compound E3 was synthesized with a yield of 56% according to Example 2-4. $^1$H NMR (400 MHz, CDCl$_3$): δ 3.95 (m, 1H), 3.88 (m, 2H), 3.71 (d, 1H), 3.55 (d, 1H), 3.37 (br s, 2H), 1.79 (m, 1H), 1.70 (br d, 1H), 1.52 (m, 2H), 1.26-0.98 (m, 42H), 0.88 (t, J=6.8 Hz, 6H); $^{13}$C NMR (100 MHz, CDCl$_3$): δ 79.47, 68.20, 63.25, 42.50, 42.40, 32.85, 32.50, 31.93, 30.95, 30.65, 29.70, 29.66, 29.53, 29.37, 22.92, 22.70, 14.12.

<7-4> Synthesis of ACA-AC12a

ACA-AC12a was synthesized with a yield of 72% according to Example 2-5. $^1$H NMR (400 MHz, CDCl$_3$): δ 8.29-7.78 (m, 24H), 7.58-7.21 (m, 36H), 6.18 (t, J=9.6 Hz, 1H), 5.92 (t, J=9.6 Hz, 1H), 5.83 (t, J=9.6 Hz, 1H), 5.77-5.55 (m, 4H), 5.50-5.38 (m, 4H), 4.64-4.37 (m, 10H), 4.31-4.29 (m, 1H), 4.23-4.20 (m, 1H), 4.01-3.96 (m, 2H), 3.87-3.84 (m, 1H), 3.79-3.73 (m, 1H), 1.78-1.74 (m, 1H), 1.69-1.56 (m, 1H), 1.29-1.06 (m, 44H), 0.88 (t, J=6.8 Hz, 6H); $^{13}$C NMR (100 MHz, CDCl$_3$): δ 166.07, 166.0, 165.87, 165.81, 165.19, 165.15, 164.79, 164.74, 133.55, 133.50, 133.43, 133.27, 133.16, 133.09, 132.99, 130.04, 129.85, 129.77, 129.66, 129.46, 128.83, 129.51, 128.43, 128.33, 101.82, 101.60, 101.23, 101.11, 101.01, 100.92, 73.21, 73.11, 72.84, 72.75, 72.31, 72.15, 72.07, 72.0, 71.89, 71.71, 71.52, 70.04, 69.91, 69.77, 69.39, 63.41, 63.31, 62.94, 62.55, 32.10, 30.68, 30.52, 29.85, 29.78, 29.71, 29.69, 29.56, 29.51, 29.79, 29.48, 23.66, 23.31, 22.75, 14.21.

<7-5> Synthesis of ACA-AC12

ACA-AC12 was synthesized with a yield of 85% according to Example 2-6. $^1$H NMR (400 MHz, CD$_3$OD): δ 4.56 and 4.51 (d, J=8.0 Hz, 1H), 4.33 and 4.23 (d, J=8.0 Hz, 2H), 4.18-4.03 (m, 3H), 3.93-3.83 (m, 4H), 3.73-3.60 (m, 4H), 3.42-3.15 (m, 14H), 2.02-1.86 and 1.77-1.68 (m, 2H), 1.48-1.16 (m, 40H), 0.90 (t, J=6.8 Hz, 6H); $^{13}$C NMR (100 MHz, CD$_3$OD): δ 105.38, 104.44, 104.27, 104.0, 81.24, 80.0, 78.38, 78.26, 78.13, 78.04, 77.98, 77.89, 77.15, 75.98, 75.78, 75.23, 75.07, 74.98, 74.48, 72.74, 72.26, 71.87, 71.71, 71.65, 71.56, 69.06, 67.61, 63.42, 63.30, 63.01, 62.84, 45.24, 44.59, 34.63, 33.11, 32.62, 32.50, 32.09, 31.98, 31.84, 30.88, 30.87, 30.83, 30.71, 30.52, 24.98, 24.59, 24.28, 23.76, 14.49; HRMS (FAB): calcd. for C$_{47}$H$_{90}$O$_{18}$Na$^+$ [M+Na]$^+$ 965.6025, found 965.6022.

<Preparation Example 8> Synthesis of ACA-AC13

<8-1> Synthesis of Compound C4

Compound C4 was synthesized with a yield of 40% according to Examples 2-1 and 2-2. $^1$H NMR (400 MHz, CDCl$_3$): δ 5.19 (s, 1H), 3.90 (s, 3H), 3.70 (s, 3H), 3.68 (s, 3H), 1.77-1.69 (m, 4H), 1.32-1.25 (m, 40H), 1.19-1.11 (m, 2H), 1.06-0.98 (m, 2H), 0.88 (t, J=6.8 Hz, 6H); $^{13}$C NMR (100 MHz, CDCl$_3$): δ 174.04, 173.62, 165.43, 96.92, 62.90, 57.38, 52.05, 51.17, 31.94, 31.91, 29.91, 29.72, 29.69, 29.67, 29.64, 29.61, 29.47, 29.41, 29.38, 23.81, 22.71, 14.14.

<8-2> Synthesis of Compound D4

Compound D4 was synthesized with a yield of 60% according to Example 2-3. $^1$H NMR (400 MHz, CDCl$_3$): δ 3.73 (s, 3H), 3.72 (s, 3H), 3.49 (s, 2H), 1.94-1.75 (m, 4H), 1.32-1.25 (m, 40H), 1.13-1.02 (m, 4H), 0.88 (t, J=6.8 Hz, 6H); $^{13}$C NMR (100 MHz, CDCl$_3$): δ 199.93, 172.60, 167.22, 63.89, 52.37, 52.33, 45.79, 31.93, 31.60, 29.90, 29.70, 29.63, 29.54, 29.41, 29.36, 29.31, 23.78, 22.71, 14.12.

<8-3> Synthesis of Compound E4

Compound E4 was synthesized with a yield of 55% according to Example 2-4. $^1$H NMR (400 MHz, CDCl$_3$): δ 3.99-3.95 (m, 1H), 3.90-3.85 (m, 2H), 3.72 (d, 1H), 3.56 (d, 1H), 2.71 (br s, 1H), 1.79 (m, 1H), 1.71 (m, 1H), 1.52 (m, 2H), 1.26-0.98 (m, 46H), 0.88 (t, J=6.8 Hz, 6H); $^{13}$C NMR (100 MHz, CDCl$_3$): δ 79.47, 68.20, 63.25, 42.50, 42.40, 32.85, 32.50, 31.93, 30.95, 30.65, 29.73, 29.70, 29.67, 29.53, 29.37, 22.93, 22.71, 14.13.

<8-4> Synthesis of ACA-AC13a

ACA-AC13a was synthesized with a yield of 60% according to Example 2-5. $^1$H NMR (400 MHz, CDCl$_3$): δ 8.28-7.77 (m, 24H), 7.60-7.21 (m, 36H), 6.17 (t, J=9.6 Hz, 1H), 5.93 (t, J=9.6 Hz, 1H), 5.82 (t, J=9.6 Hz, 1H), 5.77-5.55 (m, 4H), 5.50-5.38 (m, 4H), 4.64-4.37 (m, 10H), 4.31-4.29 (m, 1H), 4.23-4.20 (m, 1H), 4.01-3.96 (m, 2H), 3.87-3.84 (m, 1H), 3.79-3.73 (m, 1H), 1.78-1.74 (m, 1H), 1.69-1.56 (m, 1H), 1.29-1.06 (m, 48H), 0.88 (t, J=6.8 Hz, 6H); $^{13}$C NMR (100 MHz, CDCl$_3$): δ 166.07, 166.0, 165.87, 165.81, 165.19, 165.15, 164.79, 164.74, 133.55, 133.50, 133.43, 133.27, 133.16, 133.09, 132.99, 130.04, 129.85, 129.77, 129.66, 129.46, 128.83, 129.51, 128.43, 128.33, 101.82, 101.60, 101.23, 101.11, 101.01, 100.92, 73.21, 73.11, 72.84, 72.75, 72.31, 72.15, 72.07, 72.0, 71.89, 71.71, 71.52, 70.04, 69.91, 69.77, 69.39, 63.41, 63.31, 62.94, 62.55, 32.10, 30.68, 30.52, 29.85, 29.78, 29.70, 29.69, 29.56, 29.51, 29.79, 29.48, 23.66, 23.31, 22.75, 14.22.

<8-5> Synthesis of ACA-AC13

ACA-AC13 was synthesized with a yield of 82% according to Example 2-6. $^1$H NMR (400 MHz, CD$_3$OD): δ 4.56 and 4.51 (d, J=8.0 Hz, 1H), 4.33 and 4.23 (d, J=8.0 Hz, 2H), 4.18-4.03 (m, 3H), 3.93-3.83 (m, 4H), 3.73-3.60 (m, 4H), 3.42-3.15 (m, 14H), 2.02-1.86 and 1.77-1.68 (m, 2H), 1.48-1.16 (m, 44H), 0.90 (t, J=6.8 Hz, 6H); $^{13}$C NMR (100 MHz, CD$_3$OD): δ 105.38, 104.44, 104.27, 104.0, 81.24, 80.0, 78.38, 78.26, 78.13, 78.04, 77.98, 77.89, 77.15, 75.98, 75.78, 75.23, 75.07, 74.98, 74.48, 72.74, 72.26, 71.87, 71.71, 71.65, 71.56, 69.06, 67.61, 63.42, 63.30, 63.01, 62.84, 45.24, 44.59, 34.63, 33.11, 32.62, 32.50, 32.09, 31.98, 31.84, 30.88, 30.87, 30.83, 30.71, 30.52, 24.98, 24.59, 24.28, 23.76, 14.49; HRMS (FAB): calcd. for C$_{49}$H$_{94}$O$_{18}$Na$^+$ [M+Na]$^+$ 993.6338, found 993.6343.

<Experimental Example 1> Characteristics of ACAs

To check the characteristics of ACAs synthesized according to the synthesis methods of Examples 1 to 4, critical micelle concentrations (CMCs) of the ACAs and hydrodynamic diameters (DO of the formed micelles were measured.

Specifically, the critical micelle concentration (CMC) was measured by fluorescence staining using diphenylhexatriene (DPH), and the hydrodynamic diameters ($D_h$) of the micelles formed by each of the preparations (1.0% by weight) were measured by means of a dynamic light scattering (DLS) experiment. The measured results are shown in Table 1 in comparison to DDM and octyl glucoside neopentyl glycol (OGNG), two existing amphipathic molecule (detergent).

TABLE 1

| Detergent | M.W.[a] | CMC (mM) | CMC (% by weight) | $R_h$ (nm)[b] | Solubility (% by weight)[c] |
|---|---|---|---|---|---|
| ACA-SC10 | 887.1 | ~0.015 | ~0.0013 | 2.4 ± 0.2 | >10 |
| ACA-SC11 | 915.2 | ~0.010 | ~0.0009 | 2.9 ± 0.3 | ~10 |
| ACA-SC12 | 943.2 | ~0.007 | ~0.0007 | 8.3 ± 0.1 | ~10 |
| ACA-SC13 | 971.3 | ~0.005 | ~0.0005 | 13.9 ± 1.1 | ~5 |
| ACA-AC10 | 887.1 | ~0.019 | ~0.0017 | 2.7 ± 0.2 | >10 |
| ACA-AC11 | 915.2 | ~0.014 | ~0.0013 | 3.3 ± 0.2 | ~10 |
| ACA-AC12 | 943.2 | ~0.012 | ~0.0011 | 8.9 ± 0.7 | ~9 |
| OGNG[d] | 568.7 | ~1.0 | ~0.058 | 4.4 ± 0.3 | >10 |
| DDM | 510.1 | 0.17 | 0.0087 | 3.4 ± 0.3 | >10 |

[a]Molecular weight of the detergent.
[b]Hydrodynamic diameter of the micelles determined at 1.0% by weight by dynamic light scattering.

CMC values (0.0005 to 0.019 mM) of most ACAs were significantly lower compared to the CMC value (0.17 mM) of DDM. Therefore, it was confirmed that the ACAs had a higher self-assembling tendency because they easily formed micelles even at a low concentration. Also, the CMC values of the ACAs decreased with an increasing length of an alkyl chain, indicating that the hydrophobicity became higher as the length of the alkyl chain increased. In particular, the ACA-Ss had a lower CMC and a smaller micelle size compared to the ACA-As. These characteristics may be understood as the ACA-Ss having a symmetrical structure have a higher self-assembling tendency compared to the ACA-As having an asymmetrical structure. In addition, these structural characteristics were confirmed to be associated with the water solubility of each of the amphipathic compounds.

Figure 3:
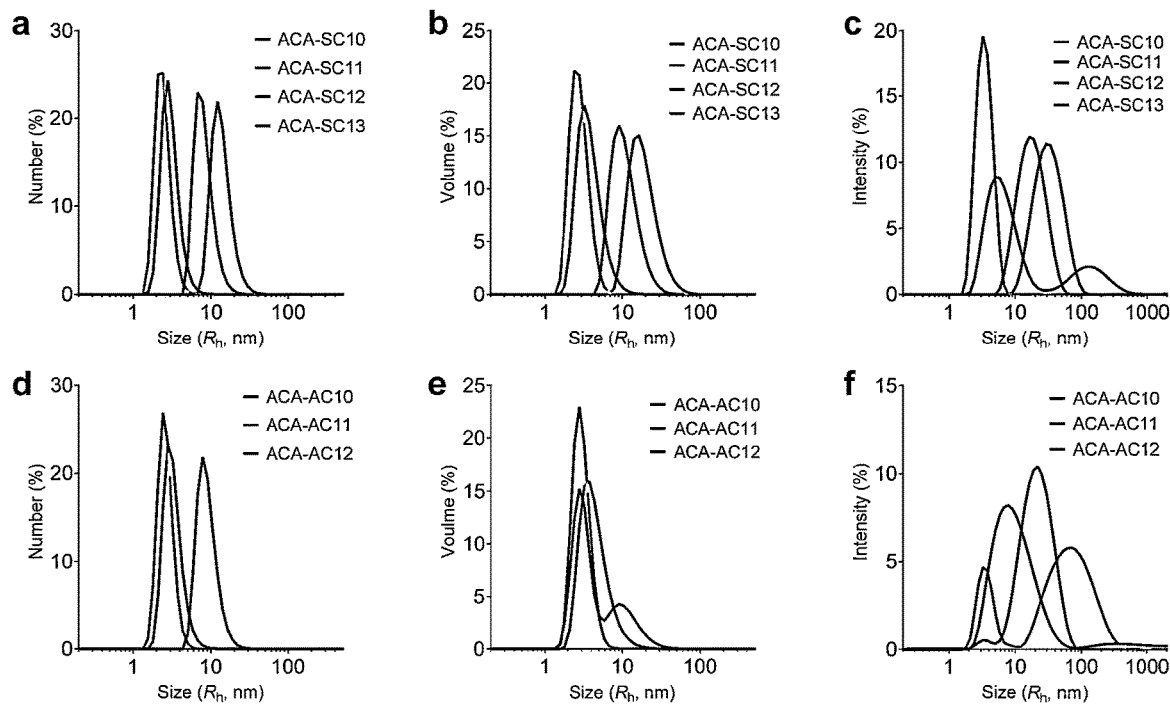
FIG. 3 is a diagram showing a size distribution of micelles formed by ACAs.

In addition, the size distribution of the micelles formed by ACAs was examined by DLS. As a result, it was confirmed that the size of the micelles increased with an increasing length of the alkyl chain. This is because a compound having a cylindrical structure easy for self-assemblage is formed as more carbon is added to the hydrophobic end (FIG. 3).

<Experimental Example 2> Evaluation of Ability of ACAs to Stabilize LeuT Membrane Protein Structure An experiment was performed to measure the structural stability of a LeuT protein by ACAs. Each of the amphipathic compounds was used at a concentration of CMC+0.04% by weight or CMC+0.2% by weight, and the substrate-binding properties of LeuT were measured by a scintillation proximity assay (SPA) using [$^3$H]-Leu. Each of the measurements was performed at room temperature at regular intervals during an incubation period of 13 days.

Specifically, Bacterial Leucine Transporter (LeuT) from *Aquifex aeolicus* was purified according to the protocol as described previously (G. Deckert, et al., Nature 1998, 392, 353-358). The cloned LeuT, C-terminally 8×His-tagged was used and inserted into the pET16p expression vector. The plasmid was transformed into *E. coli* C41 (DE3) and LeuT was expressed by the addition of 0.1 mM isopropyl b-D-thiogalactopyraniside (IPTG). To collect and isolate cell from culture surfaces, cells were incubated for 20 hrs at 20° C. followed by centrifugation for harvesting. After LeuT was solubilized in 1.0% DDM, Ni$^{2+}$-NTA resins were added and incubated for 1 h for immobilization and eluted in buffer containing 20 mM Tris-HCl (pH 8.0), 1 mM NaCl, 199 mM KCl, 0.05% DDM and 300 mM imidazole. Subsequently, 1.5 mg/mL protein stock was diluted by 10 times in an identical buffer without DDM and imidazole, but supplemented with each individual new detergent (ACA-SCs and ACA-ACs) and DDM at the final concentrations of CMC+0.04 wt % or 0.2 wt %. Protein samples were incubated for one day for detergent exchange. The detergents were evaluated at regular intervals over the course of 13-day incubation at room temperature. As for measurement of LeuT activity, 5 mL of sample were transferred to a buffer containing 20 mM Tris-HCl (pH 8.0), 200 mM NaCl and each detergent in the concentration. Protein activity was determined by the addition of 20 nM [$^3$H]-leucine and 1.25 mg/mL copper chelate (His-Tag) Ysi beads (scintillation proximity assay (SPA)). A Micro Beta liquid scintillation counter (Perkin Elmer) was used for the assessment.

Figure 4:
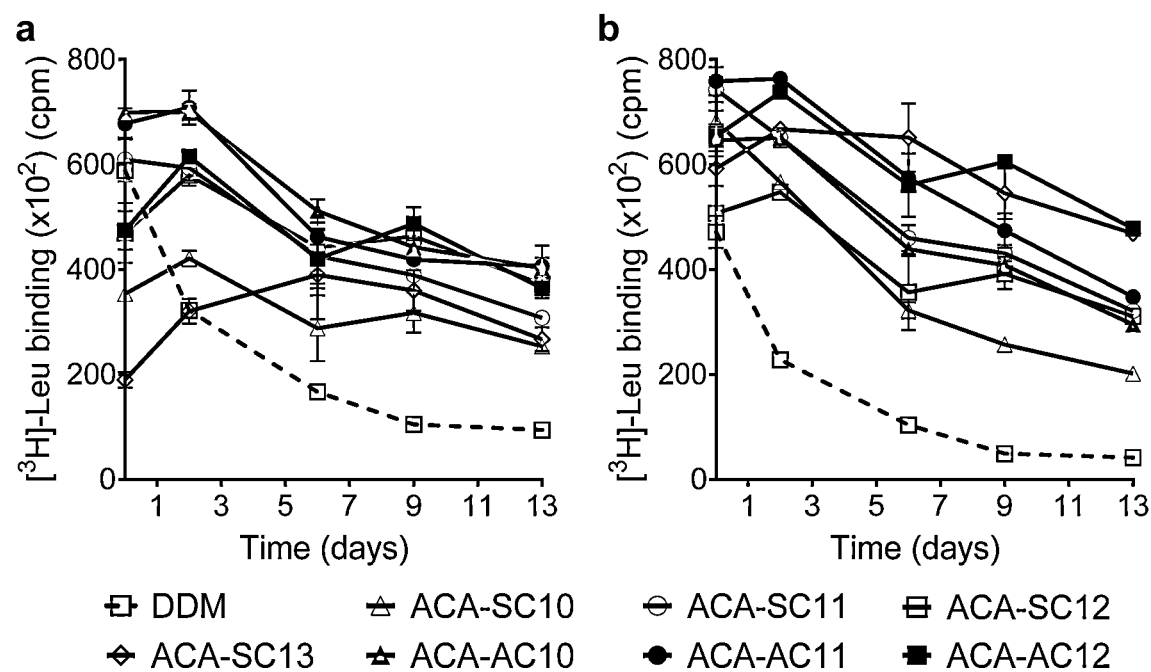
FIG. 4 shows the results of periodically measuring the structural stability of a leucine transporter (LeuT) in an aqueous solution by ACAs or DDM for 13 days at (a) CMC+0.04% by weight and (b) CMC+0.2% by weight.

As shown in FIG. 4, all the ACAs had a similar or lower initial activity compared to DDM, and had a superior effect of maintaining substrate-binding properties of LeuT for a long-term incubation period of 13 days compared to DDM. Also, it was confirmed that the effect of ACAs on LeuT stabilization was improved at an increased concentration of CMC+0.2% by weight compared to the effect of ACAs obtained at a concentration of CMC+0.04% by weight.

These results suggest that the types of the structures of ACAs and the length of the alkyl chains serve as important factors for the maintenance of the structural stability of LeuT.

<Experimental Example 3> Evaluation of Ability of ACAs to Stabilize MelB Membrane Protein Structure Melibiose and other galactoside transporter MelB was produced by *E. coli* DW2 strain (ΔmelB and ΔlacZY) harboring pK95ΔΔHB/WT MelB$_{St}$/CH10 plasmid. The plasmid contains the gene encoding the wild-type melibiose permease of Salmonella typhimurium (MelB$_{St}$) with a 10-His tag at the C-terminus. Cell growth and membrane preparation were carried out as described in A. S. Ethayathulla, et al., Nat. Commun. 2014, 5, 3009. Protein assay was carried out with a Micro BCA kit (Thermo Scientific). The membrane samples containing MelB$_{St}$ (10 mg/mL) in a solubilization buffer (20 mM sodium phosphate, pH 7.5, 200 mM NaCl, 10% glycerol and 20 mM melibiose) were mixed with each individual detergent (ACA-SCs, ACA-ACs and DDM) at 1.5% (w/v). Protein extractions were carried out at 0° C. for 90 min. The protein samples were further incubated at three different temperatures (45, 55, and 65° C.) for 90 min. After extraction and incubation, insoluble fractions were removed by ultracentrifugation at 355,590 g in a Beckman Optima™ MAX Ultracentrifuge using a TLA-100 rotor for 45 min at 4° C. 20 mg membrane proteins without ultracentrifugation and detergent extracts after the ultracentrifugation with the same volume were loaded for analysis by SDS-15% PAGE, and immunoblotting with a HisProbe-HRP antibody (Thermo Scientific) was conducted for visualizing the MelB$_{St}$.

Figure 5:
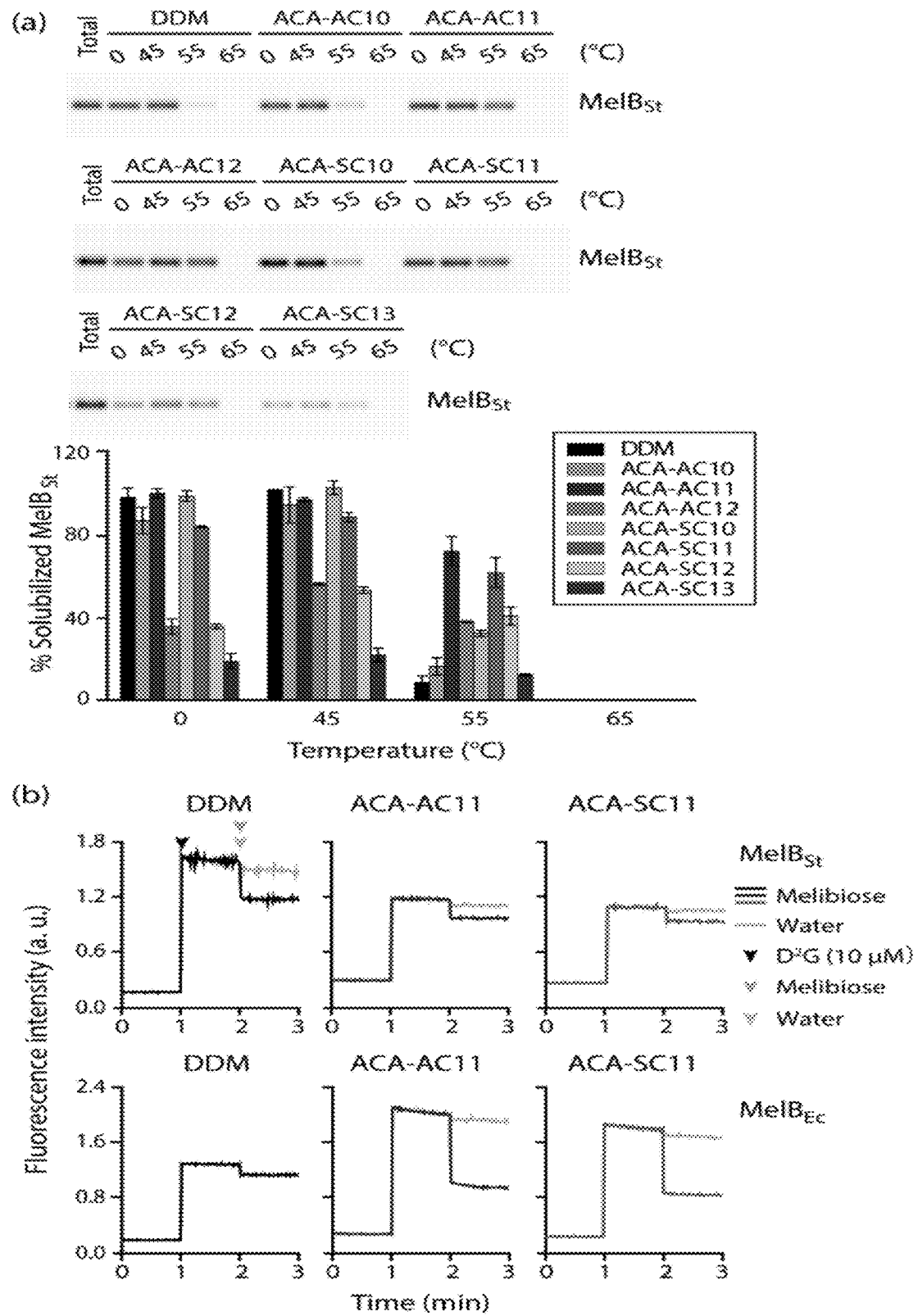
FIG. 5 shows the results of measuring a MelB protein solubilizing capacity by ACAs or DDM according to the temperature.

As shown in FIG. 5A, it was confirmed that most of the ACAs exhibited less MelB$_{St}$ protein extraction efficiency at 0° C. and 45° C. compared to DDM.

However, DDM had a markedly reduced protein solubilization ability when the temperature was increased to 55° C., but ACA-AC11 and ACA-SC11 exhibited a MelB$_{St}$ solubilization ability at approximately 70% and approximately 60%, respectively. The solubilized MelB protein was not observed at a temperature of 65° C. in both ACAs and DDM.

In general, it was confirmed that DDM had a similar or higher protein extraction efficiency at a low temperature (0° C.) compared to the ACAs, but an amount of the MelB protein solubilized by the ACAs further increased with an increasing temperature (45° C. and 55° C.). As a result, it can be seen that DDM had a rather excellent protein extraction efficiency, but ACAs had a superior ability to maintain a solubilized state of the protein, that is, a protein solubilization ability.

In addition, Trp→D$^2$G FRET analysis was performed using a (right-side-out (RSO) vesicle. Specifically, RSO membrane vesicles were prepared via osmotic lysis from *E. coli* DW2 cells containing MelB$_{St}$ or MelB$_{EC}$. The vesicles in a buffer containing 100 mM KPi (pH 7.5) and 100 mM NaCl at a protein concentration of 1 mg/ml were treated with 1.0% of individual detergents (DDM, ACA-SC11 and ACA-AC11) at 23° C. for 60 min and subjected to ultracentrifugation using TLA 120.2 rotor at >300,000 g for 45 min at 4° C. The supernatants were applied for the FRET (Trp→*D$^2$G) experiments using an Amico-Bowman Series 2 (AB2) Spectrofluorometer. The 2'-(N-Dansyl)aminoalkyl-1-thio-b-D-galactopyranoside (D$^2$G, dansylgalactoside) was obtained from Drs. Gerard Leblanc and H. Ronald Kaback. D$^2$G FRET signal was collected at 490 and 465 nm for MelB$_{St}$ and Mel$_{Ec}$, respectively, upon excitation of Trp residues at 290 nm. 10 mM D$^2$G and excess melibiose or equal volume of water (control) were added into the MelB solutions at 1-min and 2-min time points, respectively.

As shown in FIG. 5B, the addition of D$^2$G to the active MelB$_{St}$ provided a strong fluorescence signal, and the intensity of the fluorescence signal was reduced as ligand-substrate exchange occurred at a binding site when melibiose competing with D$^2$G was added thereto. The DDM-solubilized MelB$_{St}$ suitably responds to D$^2$G and melibiose when D$^2$G and melibiose were sequentially added. On the other hand, it was observed that, when a less stable homologue MelB$_{EC}$ obtained from *E. coli* was used under the same conditions, the function of the protein was completely lost. On the contrary, both of the two MelB homologues solubilized by ACAs preserved their function well. Therefore, it was confirmed that such ACAs were superior in maintaining MelB in a functional form compared to DDM.

<Experimental Example 4> Evaluation of Ability of ACAs to Stabilize β$_2$AR Membrane Protein Structure An experiment was performed to measure the structural stability of a human β$_2$ adrenergic receptor (β$_2$AR) and a G protein-coupled receptor (GPCR) by ACAs.

Specifically, b$_2$AR in 0.1% DDM was purified based on a previously reported protocol (D. M. Rosenbaum, et al., *Science*, 2007, 318, 1266-1273) and finally concentrated to around 10 mg/ml (approximately 200 mM). The DDM-purified receptor was diluted into buffer solutions containing DDM (as control), LMNG, OGNG, ACA-SC10/SC11/SC12/SC13 and ACA-AC10/AC11/AC12 to reach a final detergent concentration of 0.2 wt %. b$_2$AR in each detergent was incubated for seven days at room temperature and its ligand binding capacity was measured at regular intervals (0/1/3/7 days) during the incubation. The ligand binding ability of the receptor was measured using 10 nM of radioactive [$^3$H]-dihydroalprenolol (DHA). The [$^3$H]-DHA-containing mixture was immobilized to an anti-flag resin and the resin was collected using GF/B filter paper and scintillation fluid was added into the filter paper. Receptor-bound [$^3$H]-DHA was measured with a scintillation counter (Beckman).

Figure 6A:
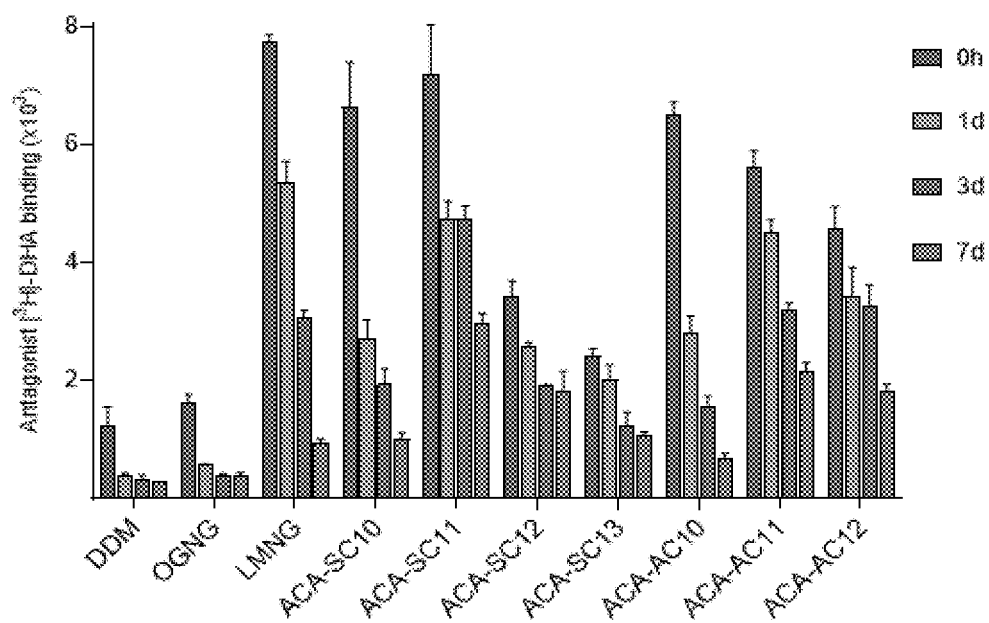
FIG. 6A shows the results of periodically measuring the structural stability of $\beta_2$AR in an aqueous solution by ACAs or DDM for 7 days at CMC+0.2% by weight.

As shown in FIG. 6A, it was confirmed that, when a test was performed to determine the initial ligand binding/maintenance properties of the receptor, most of the ACAs had an excellent ligand binding ability to the receptor compared to DDM.

Also, it was confirmed that, when a test was performed to determine the long-term ligand binding/maintenance properties to the receptor, most of the ACAs were superior in maintaining the ligand binding ability to the receptor for a long time compared to DDM.

<Experimental Example 5> MOR Heat Stability Test

To perform a long-term stability analysis, MOR in 0.1% LMNG was purified. The resulting LMNG-purified receptor was diluted into buffer solutions containing DDM (as control), LMNG, OGNG, ACA-SC10/SC11/SC12/SC13 and ACA-AC10/AC11/AC12 to reach a final detergent concentration of 0.1 wt %. MOR in each detergent was incubated for five days at 4° C. and its ligand binding capacity was measured at regular intervals during the incubation. The ligand binding ability of the receptor was measured by adding ~1 nM of radioactive [$^3$H]-diprenorphine (DPN). The [$^3$H]-DPN-containing mixture was immobilized to an anti-flag resin and the resin was collected using GF/B filter paper and scintillation fluid was added into the filter paper. Receptor-bound [$^3$H]-DHA was measured with a scintillation counter (Beckman).

Figure 6B:
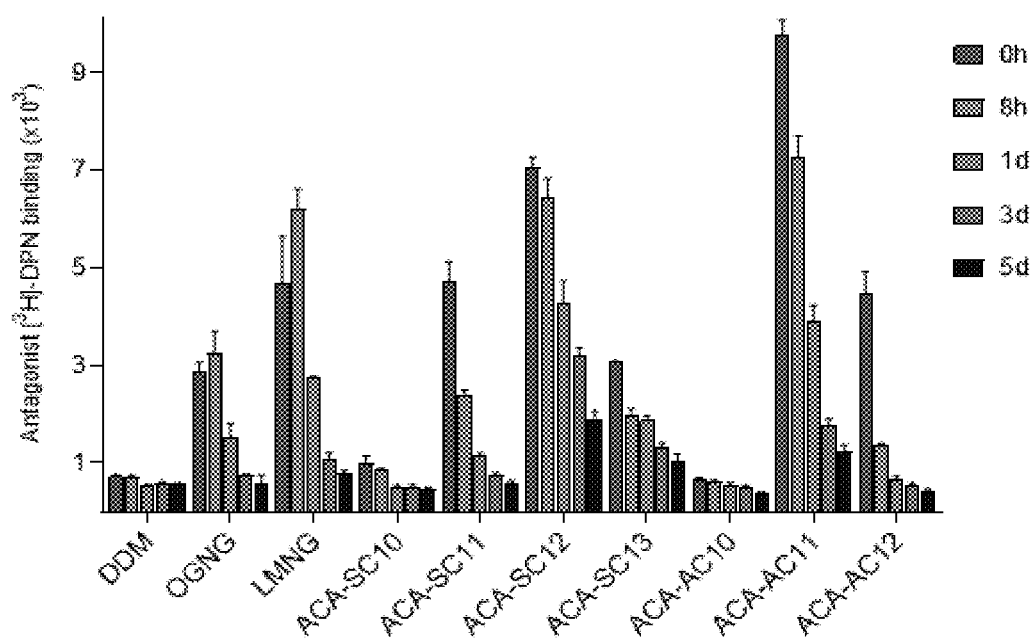
FIG. 6B shows the results of periodically measuring the structural stability of MOR in an aqueous solution by ACAs or DDM for 5 days at CMC+0.1% by weight.

As a result, the receptor solubilized in DDM lost its activity over time, and thus had a residual activity of 10% after 8 hours of the incubation. On the contrary, it was confirmed that most of the tested ACAs were significantly effective in preserving the stability of the receptor during the 5-day incubation compared to DDM. Similar to the results observed in β$_2$AR, it was confirmed that the ACAs was more effective in maintaining the MOR receptor stability for a long time compared to DDM (FIG. 6B).

What is claimed is:

1. A compound represented by the following Formula 1 or 2:

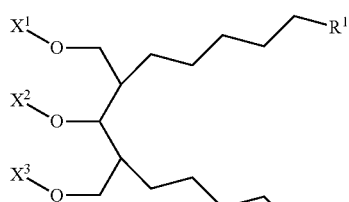

[Formula 1]

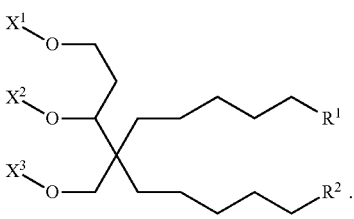

[Formula 2]

2. The compound of claim 1, wherein the saccharide is a monosaccharide or a disaccharide.

3. The compound of claim 1, wherein the saccharide is glucose or maltose.

4. The compound of claim 1, wherein $R^1$ and $R^2$ are a substituted or unsubstituted $C_3$-$C_{15}$ alkyl group; and $X^1$ to $X^3$ are glucose or maltose.

5. The compound of claim 1, wherein $R^1$ and $R^2$ are an unsubstituted $C_3$-$C_{15}$ alkyl group; and $X^1$ to $X^3$ are glucose.

6. The compound of claim 1, wherein the compound is an amphiphilic molecule for extracting, solubilizing, stabilizing, crystallizing or analyzing a membrane protein.

7. The compound of claim 1, wherein the compound has a critical micelle concentration (CMC) of 0.0001 to 1 mM in an aqueous solution.

8. A composition for extracting, solubilizing, stabilizing, crystallizing or analyzing a membrane protein, comprising the compound of claim 1.

9. The composition of claim 8, wherein the composition is a formulation of micelles, liposomes, emulsions or nanoparticles.

10. The composition of claim 8, wherein the membrane protein is a leucine transporter (LeuT), a melibiose permease (MelB), a human $\beta_2$ adrenergic receptor ($\beta_2$AR), a mouse µ-opioid receptor (MOR), or a combination of two or more thereof.

11. A method of preparing a compound represented by Formula 1, the method comprising:
 1) allowing an alkyl halide to react with a compound of Formula 3, followed by reducing the reaction product to prepare a triol compound of Formula 4 (Step 1); and
 2) introducing a saccharide to which a protecting group is attached into the compound of Formula 4 through a glycosylation reaction, followed by performing a deprotection reaction (Step 2):

[Scheme 1]

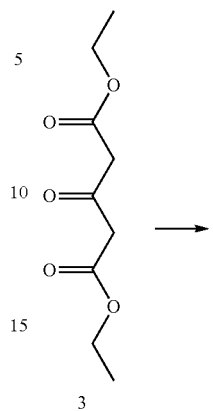

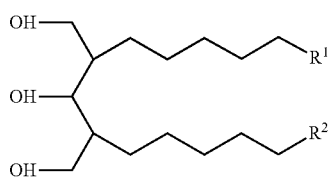

wherein:

$R^1$ or $R^2$ is a substituted or unsubstituted $C_1$-$C_{15}$ alkyl group; and $X^1$ to $X^3$ are each independently a saccharide.

12. The method of claim 11, wherein $R^1$ and $R^2$ are an unsubstituted $C_3$-$C_{15}$ alkyl group; and $X^1$ to $X^3$ are glucose or maltose.

13. A method of preparing a compound represented by Formula 2, the method comprising:
 1) subjecting a compound of Formula 3 to an enolization reaction to prepare a compound of Formula 5 (Step 1);
 2) allowing the compound of Formula 5 to react with an alkyl iodide to prepare a dialkylated compound of Formula 6 (Step 2);
 3) isomerizing the compound of Formula 6 into a keto form to prepare a compound of Formula 7 (Step 3);
 4) reducing the compound of Formula 7 to prepare a triol compound of Formula 8 (Step 4); and
 5) introducing a saccharide to which a protecting group is attached into the compound of Formula 8 through a glycosylation reaction, followed by performing a deprotection reaction (Step 5):

[Scheme 2]
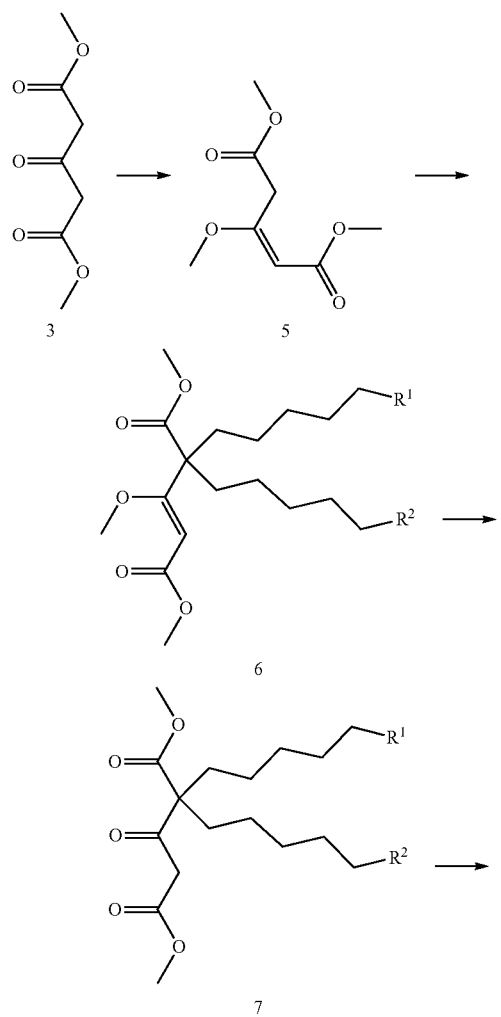
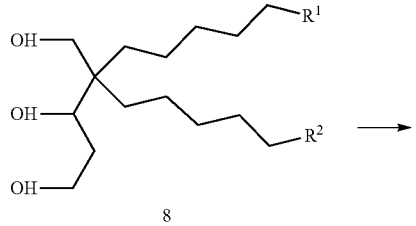
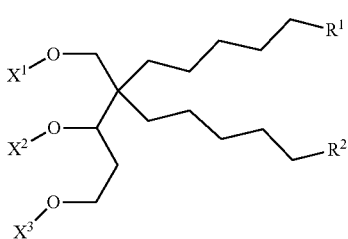
wherein:
R¹ or R² is a substituted or unsubstituted $C_1$-$C_{15}$ alkyl group; and
X¹ to X³ are each independently a saccharide.
14. The method of claim 13, wherein R¹ and R² are an unsubstituted $C_3$-$C_{15}$ alkyl group; and X¹ to X³ are glucose or maltose.
* * * * *

UNITED STATES PATENT AND TRADEMARK OFFICE
CERTIFICATE OF CORRECTION

PATENT NO. : 11,884,693 B2
APPLICATION NO. : 18/050174
DATED : January 30, 2024
INVENTOR(S) : Chae et al.

It is certified that error appears in the above-identified patent and that said Letters Patent is hereby corrected as shown below:

In the Specification

Column 8, Line 55: Please correct "Me0H." to read --MeOH.--

Column 13, Line 27: Please correct "(t, $J$ = 9.6 Hz, 11-1),"  to read --(t, $J$ = 9.6 Hz, 1H),--

Column 15, Line 64: Please correct "8 105.38," to read --δ 105.38,--

Column 17, Line 18: Please correct "(DO" to read --($D_h$)--

Column 18, Line 61: Please correct "pK95ΔΔHB/WT" to read --pK95ΔAHB/WT--

Column 19, Line 47: Please correct "(Trp→*$D^2$G)" to read --(Trp→$D^2$G)--

Signed and Sealed this
Twenty-fifth Day of June, 2024

Katherine Kelly Vidal
*Director of the United States Patent and Trademark Office*